United States Patent
Rossi (10) Patent No.: US 10,357,176 B2
(45) Date of Patent: *Jul. 23, 2019

(54) DEVICE FOR MEASURING IMPEDANCE OF BIOLOGIC TISSUES INCLUDING AN ALTERNATING CURRENT (AC) COUPLED VOLTAGE-TO-CURRENT CONVERTER

(71) Applicant: STMICROELECTRONICS S.R.L., Agrate Brianza (IT)

(72) Inventor: Stefano Rossi, Siena (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 309 days.

This patent is subject to a terminal disclaimer.

(21) Appl. No.: 15/338,674

(22) Filed: Oct. 31, 2016

(65) Prior Publication Data

US 2017/0042447 A1    Feb. 16, 2017

Related U.S. Application Data

(60) Division of application No. 14/480,024, filed on Sep. 8, 2014, now Pat. No. 9,510,768, which is a
(Continued)

(51) Int. Cl.
*A61B 5/00*      (2006.01)
*A61B 5/053*     (2006.01)
(Continued)

(52) U.S. Cl.
CPC ............ *A61B 5/053* (2013.01); *A61B 5/0537* (2013.01); *A61B 5/7225* (2013.01); *G01N 33/18* (2013.01);
(Continued)

(58) Field of Classification Search
CPC ..... A61B 5/053; A61B 5/0537; A61B 5/7228; G01N 33/18; G01N 33/48; G01R 1/30; G01R 27/02
See application file for complete search history.

(56) References Cited

U.S. PATENT DOCUMENTS

| | | |
|---|---|---|
| 3,652,930 A | 3/1972 | Sugiyama et al. |
| 4,909,261 A | 3/1990 | Rothenberg |
| (Continued) | | |

OTHER PUBLICATIONS

Ross, Alexander, et al., "Current source design for electrical impedance tomography," Physiological Measurement 24 (2003) Institute of Physics Publishing Ltd., UK, pp. 509-516. See Priority U.S. Appl. No. 14/480,024, filed Sep. 8, 2014.

*Primary Examiner* — Max F Hindenburg
(74) *Attorney, Agent, or Firm* — Slater Matsil, LLP (57) ABSTRACT

A device for measuring impedance of biological tissue may include electrodes and a voltage-to-current converter coupled to the electrodes to drive an alternating current (AC) through the tissue and sense an AC voltage. The converter may include an amplifier having first and second inputs and an output, a first voltage divider coupled to the first input, a second voltage divider coupled to the second input, a filter capacitor coupled between the output and the second voltage divider, a current limiting resistor coupled between the second input the second voltage divider, and a bypass capacitor coupled to the second input of the amplifier and in parallel with the resistor. A single-ended amplitude modulation (AM) demodulator may demodulate the AC voltage and generate a corresponding baseband voltage representing the impedance. The device may also include an output circuit to generate output signals representative of DC and AC components of the baseband voltage.

16 Claims, 9 Drawing Sheets

Related U.S. Application Data continuation-in-part of application No. 13/033,285, filed on Feb. 23, 2011, now Pat. No. 8,909,333.

(51) Int. Cl.
| | | |
|---|---|---|
| *G01R 27/02* | (2006.01) | |
| *G01R 1/30* | (2006.01) | |
| *G01N 33/18* | (2006.01) | |
| *G01N 33/48* | (2006.01) | |
| *G01N 33/483* | (2006.01) | |
| *G01R 27/26* | (2006.01) | |

(52) U.S. Cl.
CPC ......... *G01N 33/48* (2013.01); *G01N 33/4833* (2013.01); *G01R 1/30* (2013.01); *G01R 27/02* (2013.01); *G01R 27/26* (2013.01); *A61B 2562/0214* (2013.01); *Y10T 29/49007* (2015.01)

(56) References Cited

U.S. PATENT DOCUMENTS

| | | |
|---|---|---|
| 6,995,607 B2 | 2/2006 | Dosho et al. |
| 7,319,851 B2 | 1/2008 | Klumperink et al. |
| 7,761,071 B2 | 7/2010 | Miyasita et al. |
| 7,796,060 B2 | 9/2010 | Oberhuber et al. |
| 8,909,333 B2 | 12/2014 | Rossi |
| 2009/0234262 A1 | 9/2009 | Reid, Jr. et al. |
| 2011/0208028 A1 | 8/2011 | Rossi |

DEVICE FOR MEASURING IMPEDANCE OF BIOLOGIC TISSUES INCLUDING AN ALTERNATING CURRENT (AC) COUPLED VOLTAGE-TO-CURRENT CONVERTER

CROSS REFERENCE TO RELATED APPLICATIONS

This application is a divisional application of U.S. Patent Publication No. 2015/0051505 published Feb. 19, 2015, which is a continuation-in-part of U.S. Pat. No. 8,909,333 issued Dec. 9, 2014, all of which are hereby incorporated herein in their entireties by reference.

FIELD OF THE INVENTION

This invention relates to measurement instruments, and, more particularly, to a device for measuring impedance of biological tissues.

BACKGROUND OF THE INVENTION

Measurements of electrical impedance of the human body (bioimpedance) have been studied in bioengineering since the 1960s. These measurements include forcing an alternating current (AC) through the body (usually at a frequency higher than 10 kHz to avoid interference with the electrical activity of nervous and muscular tissues), and sensing the voltage drop between two points.

Water and generally all body fluids (blood, intra and extra cellular fluid, for example) provide the conductive medium of the body. Several measures and studies have been carried on applying this technique in different parts or regions of the body and using different frequencies to target different biological information (See, for example, Deok-Won Kim, Detection of physiological events by impedance, *Yonsei Medical Journal*, 30(1), 1989). In numerous applications the absolute value of the bioimpedance may be determined because it may be relatively simple to calculate it and it may provide much information. In other applications, both the modulus and phase of the complex bioimpedance may be measured.

It may be relatively difficult to determine relatively precise and reliable mathematical models of bioimpedance, particularly in thoracic regions. The main factors influencing electrical impedance in the chest may be the blood in the heart and in the aorta, and the pleural fluids and pulmonary circulation. Heart pumping, causing a variable distribution of blood in the heart-aorta region, and respiration, may be responsible for small variations of thoracic bioimpedance (i.e. the impedance of biological tissues). From these variations it may be possible to determine heart rate, breath rate, and evaluating cardiac output (volume of blood pumped by the heart for unity of time).

Figure 1:
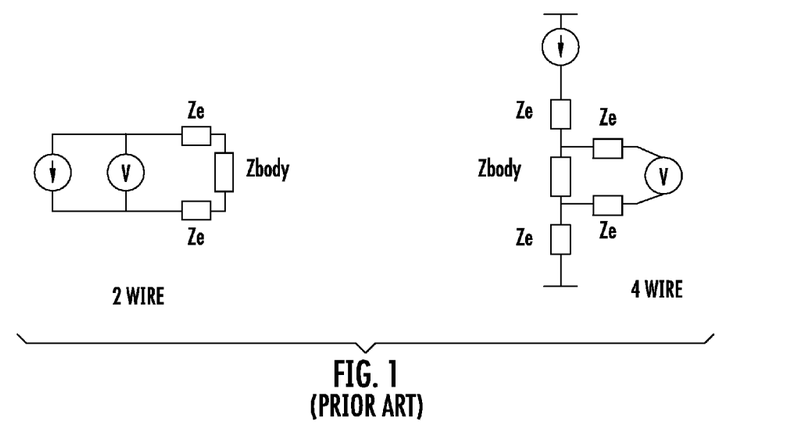
FIG. 1 schematically illustrates two architectures for measuring the impedance of a biological tissue in accordance with the prior art.

The measurements may be carried out using two or four electrodes, as schematically shown in FIG. 1. By using two electrodes, the measured impedance is the sum of the bioimpedance Zbody and of the contact impedance Ze at the electrodes. Generally, the impedance Ze disturbs the measure of the impedance Zbody. Using a four electrode setup, it may be possible to measure the impedance Zbody as the ratio between the measured voltage drop and the current forced through the body tissue with relatively more precision because the measurement may not be affected by the contact impedance Ze.

There may be a relatively strong interest in methods of carrying out this measure. Since it is a non-invasive technique, it may be correlated to a vast range of physiological parameters, thus, it may have a strong potential in many medical fields. Furthermore, the relative simplicity of the measurement, the integrability, the reduced size, and the low cost of the equipment, may make the technique of measuring thoracic bioimpedance particularly suitable to be implemented in wearable or implantable health monitoring systems.

The voltage $V_Z(t)$ sensed on the electrodes is an AC signal modulated by the bioimpedance $Z(t)$:

$$V_Z(t) = Z(t)I_0 \sin(\omega t)$$

With an AM demodulator it may be possible to obtain a baseband signal representing the modulus $|Z(t)|$ of the impedance. The phase of $Z(t)$ may be evaluated, for example, by measuring the delay between the input current and output voltage or with a phase and quadrature demodulation.

Figure 2:
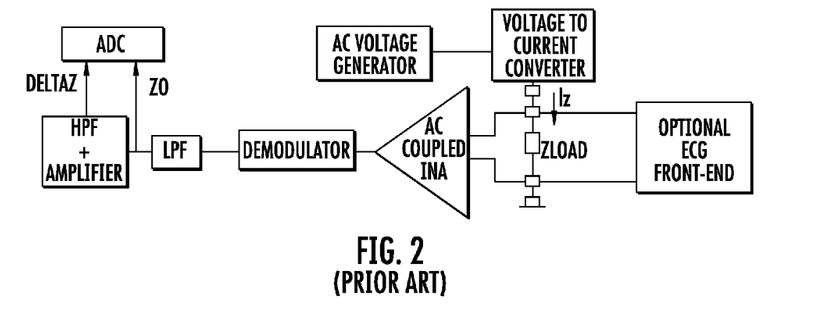
FIG. 2 schematically illustrates another architecture for measuring the impedance of a biological tissue in accordance with the prior art.

A block diagram of a typical circuit for measuring the impedance of a biological tissue is illustrated in FIG. 2. An AC voltage generated by an oscillator is used to control a voltage-to-current converter that delivers a current Iz that is injected through the biological tissue using two or four electrodes. The voltage on the biological tissue is sensed, amplified, and AM demodulated for obtaining a baseband signal. The DC component Z0 and the AC component deltaZ of the baseband signal are extracted using a low-pass filter LPF and a high-pass filter HPF and converted into digital form by an analog-to-digital converter ADC.

A sinusoidal voltage may not be used, but it may be desirable to reduce the attenuation of higher harmonics due to capacitive effects and to use an envelope detector as an AM demodulator. Furthermore the use of an adjustable sinusoidal waveform may make frequency analysis and characterization of tissues possible.

This type of system may be characterized by the presence of an instrumentation amplifier (INA) upstream from the AM demodulator. A drawback of this signal processing path is that the INA works on the modulated input signal. For this reason, the known architecture of FIG. 2 generally requires either an INA of a sufficiently large bandwidth, and, thus, has a large current consumption, or use of a low frequency for the injected current. This is a limitation because INAs, especially low power consumption and low cost devices, usually have a relatively narrow bandwidth.

Another point of the architecture of FIG. 2 is the voltage-to-current converter. It may be desirable that this circuit have a relatively large output impedance to provide negligible variations of the amplitude of the injected current when the load varies, and be DC decoupled for safety reasons, because it is desirable that DC current forced through human body tissue be less than 10 µA under normal conditions and less than 50 µA in single fault condition (See, Association for the Advanced of Medical Instrumentation. Medical electrical equipment—Part 1: General requirements for basic safety and essential performance. ANSI/AAMI ES60601-1: 2005).

Figure 3:
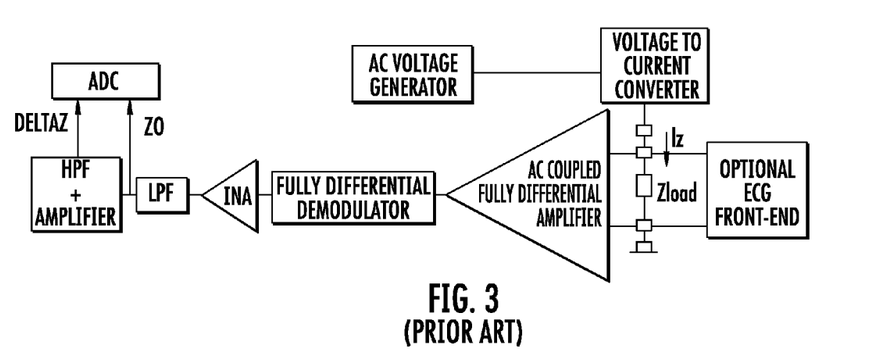
FIG. 3 schematically illustrates yet another architecture for measuring impedance of biological tissues in accordance with the prior art.

As disclosed in Rafael Gonzalez-Landaeta, Oscar Casas, and Ramon Pallas-Areny, Heart rate detection from plantar bioimpedance measurements, *IEEE Transactions on Biomedical Engineering*, 55(3):1163-1167, 2008, another known measurement system is depicted in FIG. 3. AM demodulation is performed upstream from the INA to increase the Common Mode Rejection Ratio (CMRR). The circuitry is fully differential, and a differential stage with coupled amplifiers is used as the first stage of the voltage drop on the electrodes. A high pass filter HPF and amplifier stage are used for extracting the AC components of the signal, deltaZ, that, in many applications (for example, thoracic bioimpedance measurement) includes physiological information.

The bandwidth of such a system is limited by the coupled amplifiers stage. The higher the gain (that is, greater than one), the lower the bandwidth. The working frequency used in Rafael Gonzalez-Landaeta, Oscar Casas, and Ramon Pallas-Areny, Heart rate detection from plantar bioimpedance measurements, *IEEE Transactions on Biomedical Engineering*, 55(3):1163-1167, 2008, for example, is fixed at 10 kHz, which is relatively small.

SUMMARY OF THE INVENTION

A relatively high precision device and a relative method for measuring the impedance of biological tissues using two or four electrodes has now been found. The device does not use any differential amplifier of the sensed voltage on the electrodes because it comprises a single-ended AM demodulator of the voltage towards ground on at least one sensing electrode, and an output circuit configured to generate an output signal representative of the impedance corresponding to the DC component of the baseband voltage.

According to an embodiment, the device comprises a circuit configured to force an AC current throughout the biological tissue through two electrodes. The device also includes two single-ended AM demodulators, respectively, configured to demodulate the voltages towards ground of two electrodes. The output circuit includes a differential amplifier configured to amplify the baseband demodulated single-ended voltages, and a filter for extracting the DC and the AC components of the differential baseband voltage.

According to yet another embodiment, the device comprises two single-ended AC buffers of the voltages towards ground on the electrodes. Each one of the two AM demodulators demodulate the voltage stored in a respective buffer. According to yet another embodiment, the circuit configured to force a current throughout the biological tissue is a voltage-to-current converter including an operational amplifier coupled to the electrodes and is configured to generate, on an output node, a signal representative of the voltage drop on the biological tissues.

According to yet another embodiment, the voltage-to-current converter is a Howland voltage-to-current converter controlled by an AC voltage generator. The voltage drop towards ground on an electrode may be provided on an output node of the Howland converter.

According to yet another embodiment, the voltage-to-current converter may include a DC-blocking capacitor of a DC current injected throughout the biological tissue, and a fault protection resistor configured to limit the current injected through body tissues in case of faults of the voltage-to-current converter. According to yet another embodiment, the circuit configured to force an AC current may be coupled to the electrodes through capacitors.

This disclosure also provides a Howland voltage-to-current converter configured to force a current, determined by an input voltage, through a load connected between two output terminals of the converter. The Howland voltage-to-current converter may include a first resistive voltage divider defined between a reference node and an input node configured to receive the input voltage. The Howland voltage-to-current converter may also include a second resistive voltage divider having the same voltage ratio of the first resistive voltage divider, and connected between a first output terminal of the converter and the common reference node through a DC filter capacitor. The middle terminal of the second resistive voltage divider may be a second output terminal of the converter.

The Howland voltage-to-current converter may also include an operational amplifier, an output of which is the common reference node, an input of which is connected to the middle node of the first resistive voltage divider, and the other input of which is coupled to the middle node of the second resistive voltage through a current limiting resistor.

A single op-amp voltage to current converter circuit may reach a relatively high output impedance with a GBP relatively small with respect to the working frequency is also described. This reduces the current consumption of the approach. The output impedance may be made relatively high also in the presence of a parasitic capacitance.

According to an embodiment, a particular relationship between component values has been determined. With such a relationship, the circuit exhibits the property of a very high output impedance at the working frequency, without the need of a larger bandwidth amplifier.

Another relationship for the component values has been found and is disclosed to cancel the effect of a parasitic capacitance in parallel with the load and to maintain the very high output impedance obtained with the previous relationship.

According to another embodiment, the circuit may include a bypass capacitor in a parallel to a protection resistance $R_p$ so that at the working frequency the resistance generally does not change the circuit behavior and the relationships for the component values remain valid.

According to another embodiment, the same concepts are applied to a circuit that is based upon a Howland voltage-to-current converter having a DC-blocking capacitor and a fault protection resistor with the addition of the bypass capacitance in parallel to the protection resistance $R_p$. The high output impedance and the parasitic capacitance cancellation may be obtained with the same relationships described above, for example, when $R_{4a}=0$.

According to yet another embodiment switches are added to the circuit to enable the circuit to operate at different working frequencies, selecting, for each frequency, the proper component values according to the relationships described above.

DETAILED DESCRIPTION OF THE PREFERRED EMBODIMENTS

Figure 4:
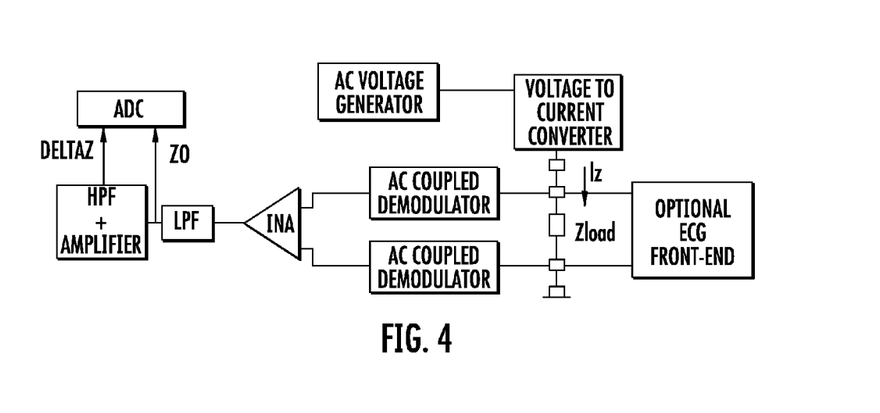
FIG. 4 schematically illustrates an embodiment of a device for measuring impedance of biological tissues in accordance with the present invention.

An embodiment of a device for measuring the impedance of biological tissue is illustrated in FIG. 4. The circuit blocks in common with the prior devices of FIGS. 2 and 3 are identified by the same labels.

The device has two single-end AM demodulators. Each demodulates the voltage towards ground of a respective electrode and generates a respective baseband signal. The demodulated baseband signals are supplied in input to an INA that generates an amplified copy of their difference.

Differently from the known device of FIG. 2, the INA amplifies a baseband signal, thus, it has a relatively large gain and a good CMRR in the baseband range of frequencies. Therefore it may be possible to use a low cost and low power consumption INA.

Differently from the prior device of FIG. 3 disclosed in Rafael Gonzalez-Landaeta, Oscar Casas, and Ramon Pallas-Areny, Heart rate detection from plantar bioimpedance measurements. *IEEE Transactions on Biomedical Engineering,* 55) 3):1163-1167, 2008, the device may not need a differential amplifier of the voltage drop sensed on the electrodes because, in the device, the AM demodulation is carried out in a single-end fashion. In a coupled amplifiers architecture, the bandwidth is reduced the more the gain is greater than one.

Preferably, the voltages towards ground of the two electrodes are read by two single ended AC coupled buffers, thus rejecting electrode offset rejection and high input impedance before being AM demodulated. This approach is preferred because unitary gain buffers have the largest bandwidth for a given operational amplifier, and, at the same time, the very good match of the unitary gain provides a good CMRR. Noise, that is a reason for which a gain in the first stages is usually preferred, is generally not an issue in this case because the first stage works on a relatively high frequency signal in a bandwidth in which the noise of common operational amplifiers is relatively low.

Any skilled person will be capable of identifying AC buffer architectures configured to be used in the device, and for this reason, they are not illustrated in detail. In a four electrode configuration, as the architecture shown in FIG. 4, an ECG front-end may optionally be coupled to measure also the electrocardiogram of a patient.

The voltage-to-current converter may be a Howland voltage-to-current converter or, more generally, any voltage-to-current converter. An exemplary voltage-to-current converter may be the converter illustrated in FIG. 6. The functioning of this exemplary converter is relatively straightforward and will not be explained in detail.

Figure 5A:
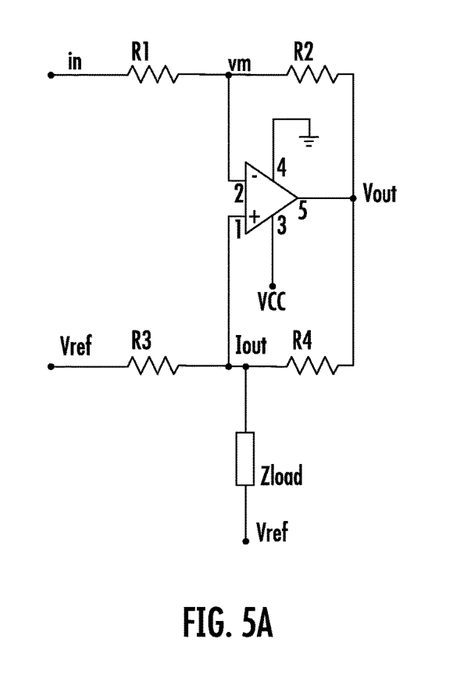
FIG. 5*a* schematically illustrates a Howland voltage-to-current converter.

Another voltage-to-current converter is the classic Howland converter illustrated in FIG. 5a. This architecture may be considered unsafe for applications on the human body because it generally does not protect the body against overcurrents due to eventual fault conditions and DC currents eventually injected throughout the body.

The load current is $$I_Z = \frac{-\frac{R_2}{R_1}(V_{in} - V_{ref})}{R_4 + \left(\frac{R_4}{R_3} - \frac{R_2}{R_1}\right)Z_{load}}$$

in which Vin is the driving voltage. If $$\frac{R_4}{R_3} = \frac{R_2}{R_1} \tag{1}$$

the current Iz is independent on the load impedance Zload. If the driving voltage Vin of the Howland circuit is an AC signal centered around the reference voltage Vref, then no DC current flows through the load. Unfortunately, this condition may not be guaranteed, for example, in the case of a single fault on the operational amplifier (i.e. one of the pins of the amplifier shorted to ground or to the supply).

Figure 5B:
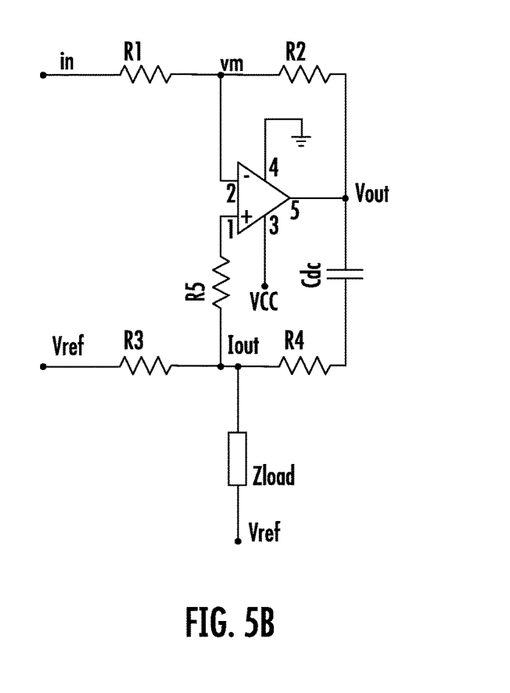
FIG. 5*b* schematically illustrates a Howland voltage-to-current converter having a DC-blocking capacitor and a fault protection resistor.

A Howland converter with protections against overcurrents and DC currents, thus configured to be used for applications on the human body, is illustrated in FIG. 5b. The capacitor blocks a DC current flowing through the load from the output of the operational amplifier, in case of a fault on the output of the amplifier or of the generator. This capacitor may not impact the normal functionality if the working frequency is much greater than 1/(Cdc·R4). The resistor R5 works as a current limiter in case of a fault on the positive input of the operational amplifier.

Figure 6:
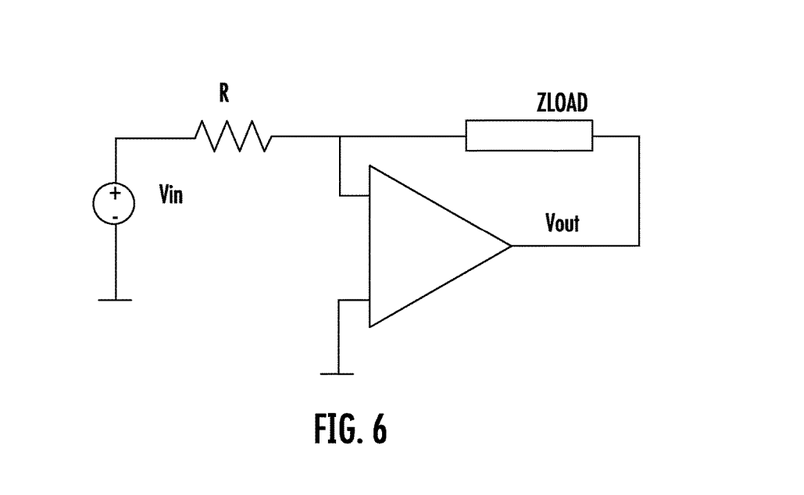
FIG. 6 schematically illustrates an exemplary voltage-to-current converter alternative to the Howland converter.
Figure 7:
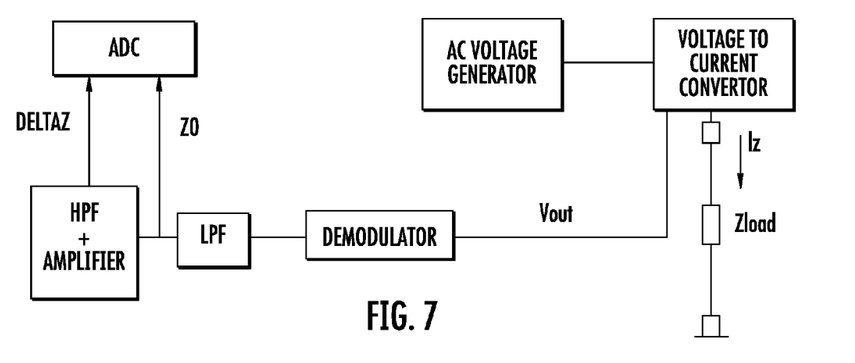
FIG. 7 schematically illustrates yet another embodiment of a device for measuring impedance of biological tissues that does not include an INA in accordance with the present invention.

The architecture of FIG. 4 may be further simplified by using the Howland voltage-to-current converter or the voltage-to-current converter of FIG. 6, or more generally, any voltage-to-current converter including an operational amplifier coupled to the electrodes and configured to generate, on an output node, a signal representative of the voltage drop on the biological tissue, in the scheme of FIG. 7. In these configurations the INA may no longer be desired because the Howland voltage-to-current converter has a relatively small output impedance. The output voltage Vout and the single-end baseband demodulated signal have an amplitude sufficient for being processed.

Even if the architecture of FIG. 7 is less precise in measuring the impedance Zload because it uses only two electrodes, it is relatively less complex, has a relatively smaller size, reduced power consumption, and reduced costs. In some applications a refined precision may not be required, for example, for sensing the breathing rate from thoracic impedance, and thus, the above architectures may conveniently be used.

The device of FIG. 7, or of FIG. 4, may not be suitable for being connected with a two lead ECG front-end as in the prior device of FIG. 3 if only two electrodes are used. This may be a limitation because, in many applications, as for measures on the human thorax, for example, the simultaneous bioimpedance and ECG recording may be useful or even desired.

Figure 8:
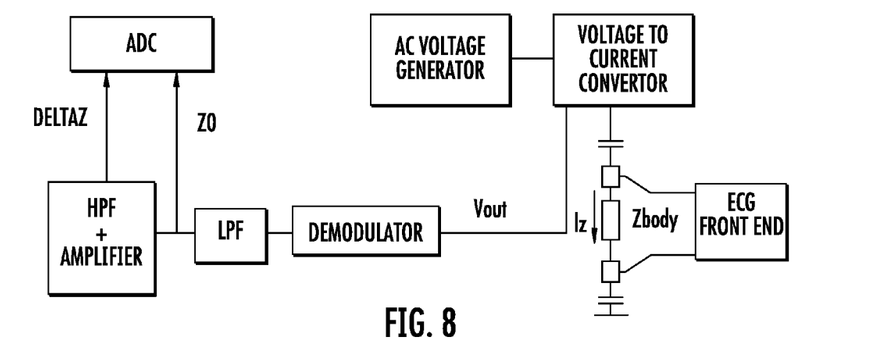
FIG. 8 schematically illustrates yet another embodiment of a device for measuring impedance of biological tissues having DC-blocking capacitors and being connected to an ECG device in accordance with the present invention.

This eventual limitation may be overcome in the device of FIG. 8. Two capacitors have been added to decouple, at low frequencies, the electrodes from the voltage-to-current converter. The impedance of capacitors sums up to the impedance of electrodes and to the bioimpedance, and may alter measurements. For this reason, it is desirable that the value of the capacitors be large enough to give an acceptably small impedance at the working frequency. On the other hand, it is desirable that the capacitors not be too large, otherwise this may cause an attenuation of the ECG.

Moreover, the frequency of the pole associated with the capacitors depends on unknown parameters, such as, for example, electrode to skin contact impedance and body impedance. For this reason, the choice of the value of capacitors may be of a particular importance.

Appropriate values of these capacitors may range from 1 nF to 100 nF, if the thoracic impedance is to be measured. Different values may be chosen depending on the particular application for which the device is designed.

Figure 9:
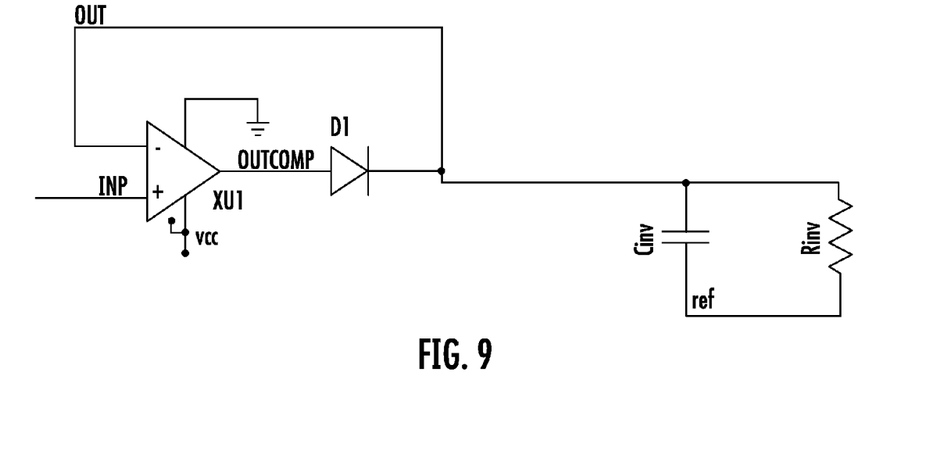
FIG. 9 schematically illustrates an AM demodulator configured to be used in the device for measuring impedance of biological tissues in accordance with the present invention.

The AM demodulator used in the device may be of any kind. According to a preferred embodiment, the AM demodulator is as illustrated in FIG. 9. It includes an envelope demodulator D1-Cinv-Rinv and a comparator XU1 that generates a logic comparison signal OUTCOMP as the result of the comparison between the input signal INP to be AM demodulated and the output signal OUT.

Differently from commonly used AM demodulators, the demodulator of FIG. 9 has a feedback comparator instead of an operational amplifier. This causes the output of the comparator to oscillate as long as the input signal attains its peak value. Then the diode becomes reversely biased, and the output of the comparator switches low. This may not significantly alter the demodulated voltage because the output low-pass filter cut-off frequency is much lower than the bandwidth of these spikes. When the input voltage INP increases, the output of the comparator almost immediately switches high.

By contrast, if an operational amplifier were used instead of the comparator XU1, the output recovery time after saturation and the slew-rate of the amplifier would limit the speed with which the signal OUTCOMP switches high. As a consequence, it may not be possible to demodulate AM signals at relatively high frequencies unless a relatively expensive and power consuming high frequency operational amplifier is used.

The AM demodulator of FIG. 9 thus may be conveniently employed in many applications where demodulation of high frequency AM signals is desired. The devices may be integrated in small packages and may operate in a range of frequencies up to 100 kHz with a relatively small power consumption (about 2.5 mW). However, this is just an example, since higher working frequencies may be obtained using faster components in the voltage to current converter and demodulator stages.

These characteristics make the devices suitable for a vast range of bioimpedance measures and applications. The flexibility and reduced dimensions may make it ideal for wearable applications, both in a clinical environment or in home monitoring tasks, such as, a band-aid, a T-shirt, or a bangle. Examples of measurements that may be carried out with the devices are the monitoring of breath rate, heart rate, and other heart related parameters in thoracic bioimpedance, body composition analysis, or local impedance measures in limbs. When relatively high precision measures are desired, the four electrode architecture may be preferred.

Figure 10:
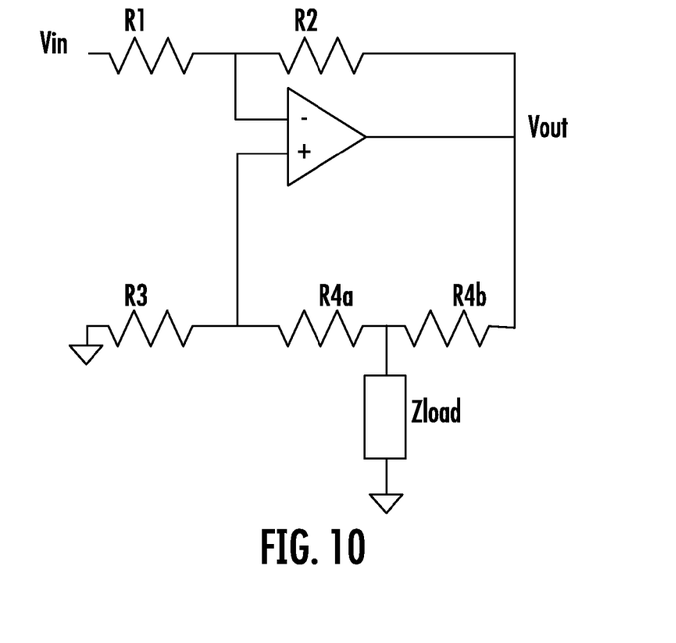
FIG. 10 schematically illustrates a voltage to current converter known as improved Howland circuit.
Figure 11:
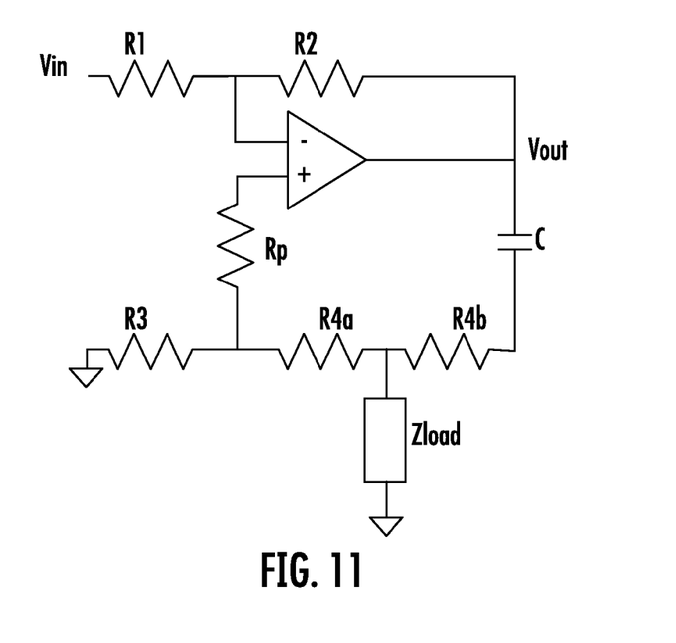
FIG. 11 schematically illustrates a voltage to current converter.

Referring now to FIGS. 10 and 11, the voltage to current converter may be a relatively important block of such a device for measuring impedance of biologic tissues, and it is present in FIGS. 4, 7 and 8. A possible implementation is illustrated in FIG. 5A. As noted above, to achieve a higher level of safety, the circuit of FIG. 5B was suggested.

An improved version of the circuit illustrated in FIG. 5A is illustrated in FIG. 10. The same concept illustrated in FIG. 5B may be applied to the circuit of FIG. 10 obtaining the circuit of FIG. 11 which presents a higher level of safety.

For these circuits the Howland condition becomes:

$$\frac{R_2}{R_1} = \frac{R_{4a} + R_{4b}}{R_3} \tag{2}'$$

while the condition described above requiring the working frequency $f_0$ to be much higher than $$\frac{1}{2\pi R_4 C}$$

is translated for the circuit of FIG. 11 into:

$$f_0 \gg \frac{1}{2\pi R_{4b} C} \tag{3}$$

A relatively important parameter for the voltage to current converter is the output impedance. Since the frequency of the exciting current is usually greater than 10 kHz, and may be, for example, some MHz, it may not be relatively easy to achieve relatively good output impedance for the V/I converter.

Figure 12:
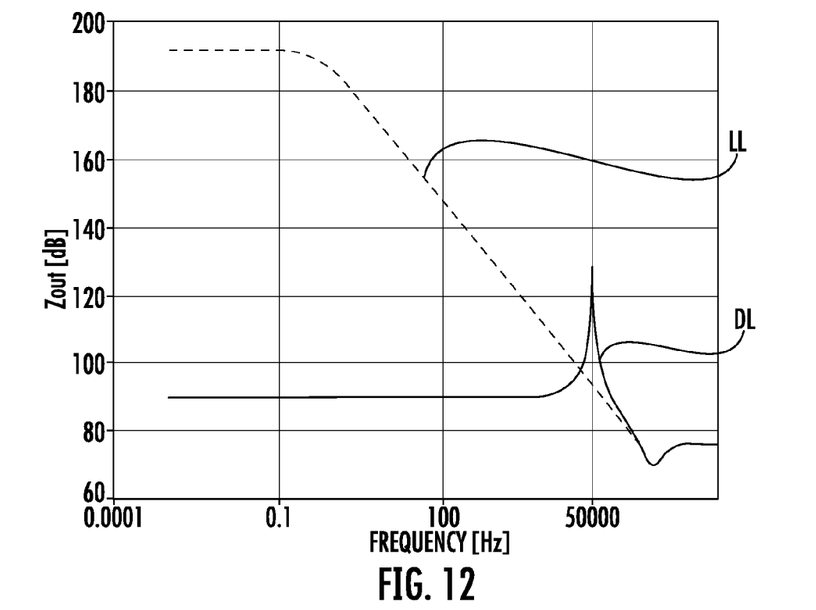
FIG. 12 is a graph of frequency versus output impedance illustrating the decreasing of the output impedance of a Howland circuit with the increasing of the frequency and output impedance significantly increasing at the working frequency.

The limited gain-bandwidth product (GBP) of the operational amplifier constitutes a main problem for determining the decreasing of the output impedance with frequency (See, for example, LL in FIG. 12). The use of a wide bandwidth amplifier is usually desired. In general, circuits with higher bandwidth generally require, with the same technologies and topologies, a higher current consumption.

This is not the only issue: parasitic capacitances in parallel with the output of the V/I converter often become the bottleneck, and it happens to reach excellent theoretical impedances which are not met in practical implementations. For this reason, the cancellation of parasitic capacitance through a negative impedance converter (NIC) has been also proposed (See A. S. Ross, G. J. Saulnier, J. C. Newell1, and D. Isaacson, "Current source design for electrical impedance tomography," *Physiological Measurements*, vol. 24, pp. 509-516, 2003). However, this still requires GBP that is relatively higher than the working frequency and an increased number of operational amplifiers.

In some applications, like the emerging one related to wearable sensors for healthcare monitoring, the additional power consumption may be relatively important. Even limiting the working frequency in the range of tens of kHz, the approaches proposed in literature usually use op-amps with a gain-bandwidth product (GBP) of, at least, tens of MHz up to GHz and, since the GBP of an op-amp is generally proportional to current consumption, this is translated in supply currents in the range of some mA. Furthermore, many approaches require more than one op-amp to work, increasing the overall supply current for the circuit.

It may be relatively important to highlight that circuits of FIG. 5B and of FIG. 11, dimensioned as described above and in equations (2) and (3) respectively, generally suffer from the same issues described above.

A person having ordinary skill in the art may readily recognize based upon the description herein and the circuit of FIG. 10, the circuit of FIG. 11. In general, this circuit suffers from the limitations described above. Nevertheless, a particular configuration has been determined which enables a very high output impedance to be reached at the working frequency.

Figure 13:
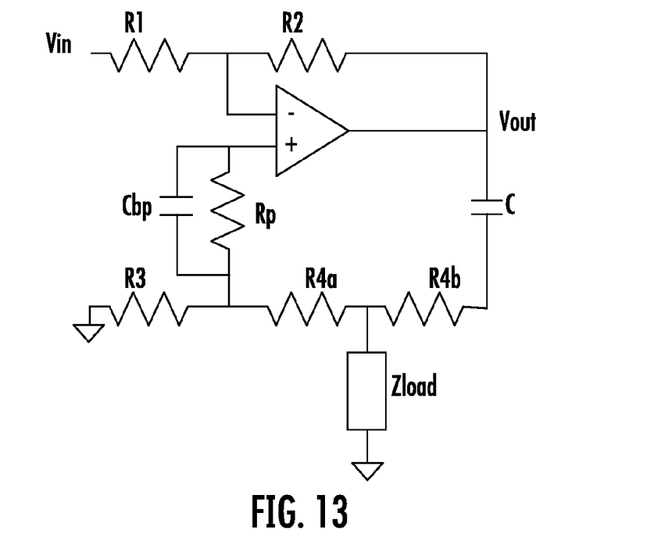
FIG. 13 schematically illustrates a circuit for obtaining a relatively high output impedance at the working frequency and the cancellation of a parasitic capacitance effect according to an embodiment of the present invention.
Figure 16:
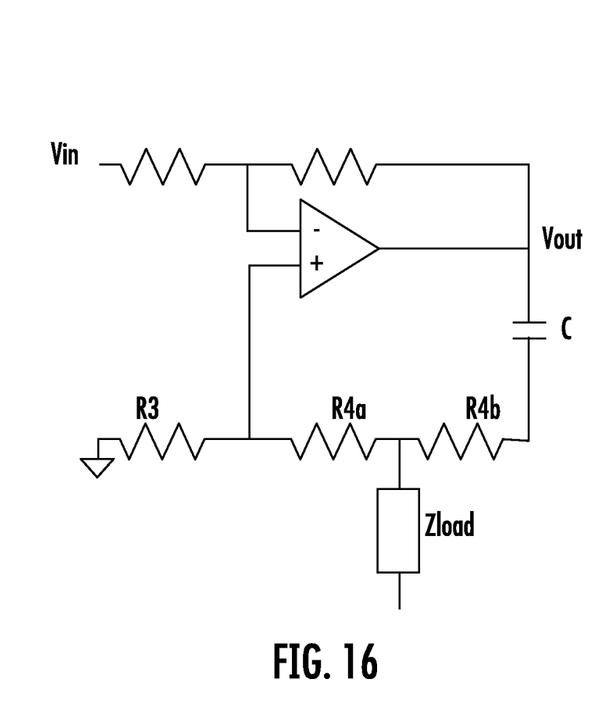
FIG. 16 is a schematic diagram of a voltage-to-current converter to which dimensioning criterion according to the present invention may be applied.

The particular configuration which is described below is applied to the general circuit of FIG. 16. The protection resistor $R_p$ in FIG. 11 (and in FIG. 5B) can disturb the effect obtained by the particular configuration that is described below. Of course it would be possible to protect the load in a different way to maintain the protection resistor $R_p$. For example, a bypass capacitor is added in parallel to $R_p$ as illustrated in FIG. 13. Such a bypass capacitor is to be chosen according to:

$$f_0 \gg \frac{1}{2\pi R_p C_{bp}} \quad (4)$$

in which $f_0$ indicates the working frequency and $C_{bp}$ is a value of the bypass capacitor. In this way, at the working frequency, circuits of FIG. 16 and of FIG. 13 become equivalent with excellent approximation, and all the following considerations apply in the same way to both the circuits.

The Howland condition expressed by EQ. 2 is still satisfied. The capacitor C, instead, is used in a different way. Its function was typically DC-blocking in the previous circuit (s), and its value was chosen according to EQ. 3, which means that the pole of the capacitor must generally be much lower than then the working frequency. In the embodiments described herein, instead, the pole of the capacitor is used to obtain a resonance effect with the first pole of the op-amp in order to have a couple of complex and conjugate poles at the working frequency, as illustrated by the line DL in FIG. 12. The synthesis of the right circuit parameters is not simple, since it involves the modeling of the amplifier as non-ideal, and the first pole must be considered in the calculations. Referring to FIG. 13, the output impedance $Z_{out}$ is the impedance seen by a test generator connected in place of the load $Z_{load}$ and its expression results:

$$Z_{out} = (R_3 + R_{4a}) \frac{(1 + R_{4b}Cs)\left(1 + \frac{s}{\omega_p}\right)}{1 + \left[\frac{1}{\omega_p} - (k_1 - k_2)R_3C\right]s + \frac{k_2 R_3 C}{\omega_p}s^2} \quad (5)$$

in which $$k_1 = 1 + \frac{R_2}{R_1},$$

$$k_2 = 1 + \frac{R_{4a} + R_{4b}}{3}$$

and $$\omega_p = \frac{\omega_{GBP}}{k_1}$$

is the pole of the non-inverting amplifier with feedback $R_2$ and $R_1$. The poles of $Z_{out}$ can be made complex and conjugate. The pulsation of the complex conjugate poles is:

$$\omega_0 = \sqrt{\frac{\omega_p}{k_2 R_3 C}} = \sqrt{\frac{\omega_{GBP}}{k_1 k_2 R_3 C}} \quad (6)$$

For example with the typical assumption of the Howland circuit expressed by EQ. 2, it is $k_1 = k_2$, and complex and conjugate poles are obtained satisfying the condition $$Q = \frac{\omega_p}{\omega_0} = \sqrt{\omega_{GBP} R_3 C} \quad (7)$$

which result in a quality factor:

$$\omega_{GBP} > \frac{1}{4R_3 C}$$

The GBP still plays a role: the DC impedance is determined by $R_3 + R_{4a}$, while, once that $\omega_0$ has been fixed, the quality factor may generally only depend on the value of $\omega_p$ which is influenced by the GBP. For small values of $k_1$ and $k_2$ (they are always greater than one), $\omega_p \approx \omega_{GBP}$ and a relatively good Q, (and so a good increase of the impedance at working frequency) can be obtained also with an op-amp with bandwidth between 10 and 100 times of the working frequency.

The $Z_{out}$ expression also presents a couple of zeros, and they act at frequency higher than $\omega_0$, otherwise they would mitigate or cancel the effect of the poles. This condition is expressed by EQ. 7 for the zero located at $\omega_p$ and, for the other one, by:

$$\frac{1}{R_{4b}C} \gg \omega_0 \quad (8)$$

Figure 14:
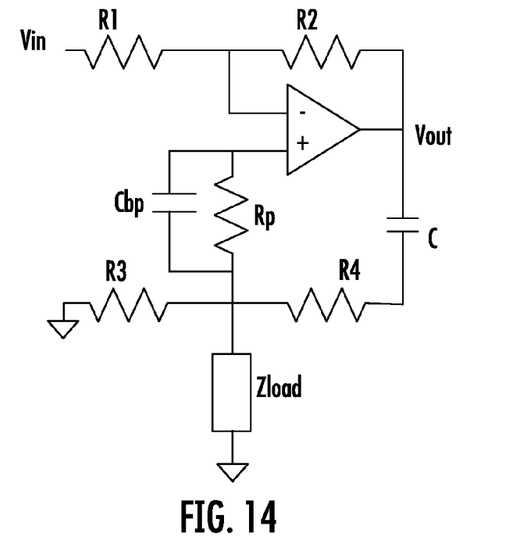
FIG. 14 schematically illustrates another circuit for obtaining a relatively high output impedance at the working frequency and the cancellation of parasitic capacitance effect according to an embodiment of the present invention.

EQ. 8 becomes $$\frac{1}{R_4 C} \gg \omega_0$$

for the circuit of FIG. 14. It may be important to highlight that this condition is reversed with respect to the one expressed by EQ. 3 which was related to the embodiments described above. This is because in those embodiments, at the working frequency, the circuit was made equivalent to the Howland one. In this embodiment, instead, the capacitance C is used to change the properties of the circuit and to obtain higher output impedance than the previous versions.

In FIG. 12 the output impedance obtained by the standard Howland circuit is illustrated by the line LL. The output impedance quickly falls down and, if a low power narrow bandwidth op-amp is chosen, the impedance at the working frequency (for example, 50 kHz is selected as illustrated) is relatively low. The same effect is present in the circuit in the embodiments described above: since EQ. 2 is valid, the impedance behavior at the working frequency is the same. The capacitance, used according to EQ. 6, instead, allows the reaching of significantly higher output impedance at the working frequency as illustrated by the line DL.

The complete frequency response $$H(j\omega) = \frac{I_l}{V_{in}}$$

is, for this circuit, different from the one described with respect to the embodiments above. The results are complex and involve all the parameters of the circuit. In general, since the output impedance is very high only at the working frequency, the frequency response also depends on $Z_{load}$. Nevertheless, to dimension the circuit, it is generally enough to calculate it at the working frequency $\omega_0$, for which the impedance is very high. With this assumption the frequency response can be considered independent on the load and can be calculated in the particular case $Z_{load}=0$ for which the circuit results simplified:

$$H(j\omega_0) = \frac{(1-k_1)Cj\omega_0}{(1+jR_{4b}C\omega_0)\left(1+j\frac{\omega_0}{\omega_p}\right)} \approx (1-k_1)Cj\omega_0 \quad (9)$$

in which the approximation is the same already discussed about the zeros of $Z_{out}$.

Since all the parameter results are correlated, the proper design of the circuit is not obvious. Anyway there are enough degrees of freedom to satisfy, at the same time, equations 6, 7, 8 and 9. A first consideration to properly define the circuit parameters is that resistors $R_3$ and $R_{4a}$ should be large to increase $Z_{out}$, improve the output swing and reduce power consumption. On the other side if they are too large a very small C may be desired to properly design $\omega_0$, and this would impact current amplitude (EQ. 9). Thus, a compromise about their order of magnitude is desirable. Once an op-amp with a gain-bandwidth produce is given, a proper design can be obtained following these steps:

once the working frequency is defined, Q can be obtained fixing $k_1$ (and $k_2$); Q defines the amplitude of the peak in the expression of the output impedance and it can be increased only reducing $k_1$ and $k_2$ (which in any case are greater than one) or selecting a different op-amp with a higher gain-bandwidth product;

$\omega_0$ can be placed at the desired value adjusting $R_3$ and C; and the proper amplitude for the current can be chosen adjusting the amplitude of $V_{in}$.

The presence of a parasitic capacitance in parallel with the output is an effect typical of practical realization of a voltage to current converter. At least a few pico-Farads can be quite common in standard PCB technology, and this can strongly decrease the output impedance of the converter. The approach allows the compensation of the effect of a parasitic capacitance.

With a parasitic capacitor $C_p$ in parallel to the output, the overall output admittance becomes $$\frac{1}{Z_{out}} + C_p s$$

in which $Z_{out}$ is reported in EQ. 5. An approximated analysis can be done, remembering that the zeros must be at high frequency (EQ. 8). In this way $C_p$ adds a first order term $(R_3+R_{4a})C_p s$ and the new Q becomes:

$$Q \approx \frac{1}{\omega_0 \left[\frac{1}{\omega_p} - (k_1 - k_2)R_3 C + (R_3 + R_{4a})C_p\right]} \quad (10)$$

so making:

$$(k_1 - k_2) \approx \frac{(R_3 + R_{4a})C_p}{R_3 C} \quad (11)$$

it is possible to restore the original quality factor of EQ. 7 and the circuit still provides relatively high output impedance.

It may be particularly important to highlight that it is generally not necessary that the relations above are exactly satisfied: it is enough to reduce the residual term added to $$\frac{1}{\omega_p}$$

as much as possible. This makes the use of a mismatch between $k_1$ and $k_2$ a viable approach, since the exact value of $C_p$ may be unknown, but an estimation is enough.

All the considerations done can be extended to the circuit of FIG. 14 assuming $R_{4a}=0$ and $R_4=R_{4b}$.

The working principle of the circuit intrinsically makes it suitable to work with a fixed frequency. A multi-frequency extension, anyway, can be obtained with the circuit showed in FIG. 15. The switches S11-S1$n$ and S21-S2$n$ allow adjusting C and $R_{4b}$ to tune the frequency, and $R_2$ to tune the resistor ratio accordingly to EQ. 5 or EQ. 11, in case a parasitic capacitance is to be cancelled.

Each terminal of the switch is connected to ground through a parasitic capacitance which is desirable to be kept as small as possible to avoid interferences with the circuit working principle.

Figure 15:
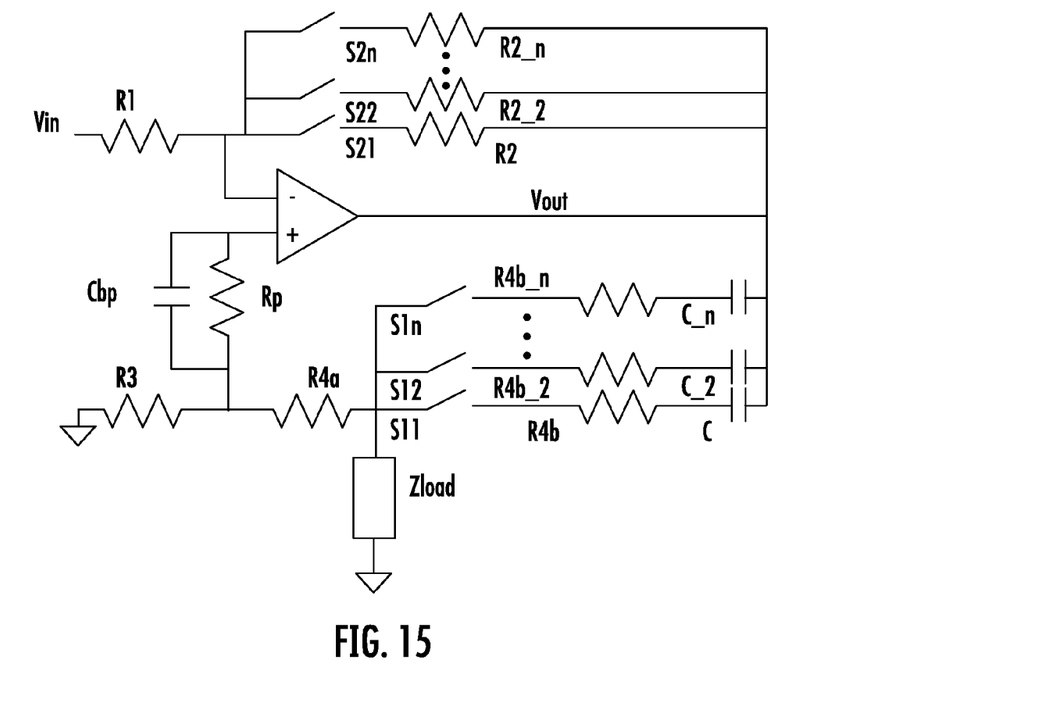
FIG. 15 schematically illustrates another circuit for operation at different selectable working frequencies in accordance with an embodiment of the present invention.

The shown distribution of switches, anyway, is chosen to reduce or minimize the effect of parasitic capacitance associated to them. With the choice shown in the picture, the branches connected to the open circuit path results in a ground connection through parasitic capacitance. They did not interfere with the circuit since they are driven directly by the amplifier output. Parasitic capacitance is present in parallel to $Z_{out}$, but its effect can be cancelled if desired, as already discussed.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed:

1. A voltage-to-current converter for a device for measuring impedance of biological tissue, the device comprising a pair of electrodes for contacting the biological tissue, at least one single-ended amplitude modulation (AM) demodulator configured to demodulate an AC voltage and to generate a corresponding output voltage representing the impedance, the voltage-to-current converter comprising:
    an amplifier to be coupled to the pair of electrodes and configured to drive an alternating current (AC) through the biological tissue and to sense an AC voltage, said amplifier having a first input, a second input, and an output;
    a current limiting resistor coupled to said second input; and
    a bypass capacitor coupled to the second input of said amplifier and in parallel with said current limiting resistor.

2. The voltage-to-current converter of claim 1, further comprising:
    an output node;
    an input node configured to receive an AC drive voltage;
    a first resistive voltage divider having a middle terminal and coupled between the output node and the input node; and
    a second resistive voltage divider having a middle terminal and a same voltage ratio as said first resistive voltage divider, and coupled between a common terminal with one of said pair of electrodes and to the output node, and another one of said pair of electrodes being coupled to the middle terminal;
    said first input of said amplifier coupled to the middle node of said first resistive voltage divider, and said second input of said amplifier coupled to the middle terminal of the second resistive voltage divider through said current limiting resistor.

3. A voltage-to-current converter for a device for measuring impedance of biological tissue, the device comprising a pair of electrodes for contacting the biological tissue, at least one single-ended amplitude modulation (AM) demodulator configured to demodulate an AC voltage and to generate a corresponding output voltage representing the impedance, the voltage-to-current converter comprising:
    an amplifier to be coupled to the pair of electrodes and configured to drive an alternating current (AC) through the biological tissue and to sense an AC voltage, said amplifier having a first input, a second input, and an output;
    a first resistive voltage divider coupled to the first input;
    a second resistive voltage divider coupled to the second input; and
    a direct current (DC) filter capacitor coupled between the output of said amplifier and said second resistive voltage divider;
    wherein for a given working frequency of said amplifier, values of said first and second resistive voltage dividers and said DC filter capacitor are chosen according to:

$$\omega\_o = \sqrt{(\omega\_p/(k\_2R\_3C))} = \sqrt{(\omega\_GBP/(k\_1k\_2R\_3C))}$$

wherein ωo is the given working frequency, $R_3$ is a resistive value of a first resistor of said second resistive voltage divider, C is a value of said DC filter capacitor, k2=1+((R$_4$a+R$_4$b)/R$_3$) wherein R$_4$a and R$_4$b are respective resistive values of second and third resistors of said second resistive voltage divider, and ωGBP=ωpk1 is a gain-bandwidth product of said amplifier, wherein k1=1+(R2/R1), and wherein R1 and R2 are respective resistive values of first and second resistors of said first resistive voltage divider.

4. The voltage-to-current converter of claim 3, wherein k1 is equal to k2.

5. The voltage-to-current converter of claim 3, wherein values of said first and second resistive voltage dividers and said DC filter capacitor are chosen according to:
    wherein Cp is a parasitic capacitance.

6. The voltage-to-current converter of claim 3, further comprising:
    an output node; and
    an input node configured to receive an AC drive voltage;
    said first resistive voltage divider having a middle terminal and being coupled between the output node and the input node; and
    said second resistive voltage divider having a middle terminal and a same voltage ratio as said first resistive voltage divider, and being coupled between a common terminal with one of said pair of electrodes and to the output node, and another one of said pair of electrodes coupled to the middle terminal;
    said first input of said amplifier coupled to the middle node of said first resistive voltage divider, and said second input of said amplifier coupled to the middle terminal of the second resistive voltage divider.

7. The voltage-to-current converter of claim 3, further comprising:
    a current limiting resistor coupled between the second input of said amplifier and said second resistive voltage divider; and
    a bypass capacitor coupled to the second input of said amplifier and in parallel with said current limiting resistor.

8. A method of making a voltage-to-current converter for a device for measuring impedance of biological tissue, the device comprising a pair of electrodes for contacting the biological tissue, at least one single-ended amplitude modulation (AM) demodulator configured to demodulate an AC voltage and to generate a corresponding output voltage representing the impedance, the method comprising:
    coupling an amplifier to the pair of electrodes to drive an alternating current (AC) through the biological tissue and to sense an AC voltage, the amplifier having a first input, a second input, and an output;
    coupling a first resistive voltage divider to the first input;
    coupling a second resistive voltage divider to the second input; and
    coupling a direct current (DC) filter capacitor between the output of amplifier and second resistive voltage divider;
    wherein for a given working frequency of the amplifier, values of the first and second resistive voltage dividers and the DC filter capacitor are chosen according to:

wherein ωo is the given working frequency, $R_3$ is a resistive value of a first resistor of the second resistive voltage divider, C is a value of the DC filter capacitor, k2=1+((R4a+R4b)/R3) wherein $R_4a$ and $R_4b$ are respective resistive values of second and third resistors of the second resistive voltage divider, and ωGBP=ωpk1 is a gain-bandwidth product of said amplifier, wherein k1=1+(R2/R1), and wherein R1 and R2 are respective resistive values of first and second resistors of the first resistive voltage divider.

9. The method of claim 8, wherein k1 is equal to k2.

10. The method of claim 8, wherein values of the first and second resistive voltage dividers and the DC filter capacitor are chosen according to:

wherein Cp is a parasitic capacitance.

11. The method of claim 8, further comprising:
coupling a middle terminal of the first resistive voltage divider between an output node and an input node for receiving an AC drive voltage;
coupling a middle terminal of the second resistive voltage divider between a common terminal with one of the pair of electrodes and to the output node, and coupling another one of the pair of electrodes to the middle terminal, the second resistive voltage divider having a same voltage ratio as the first resistive voltage divider; and
coupling first input of the amplifier to the middle node of the first resistive voltage divider and coupling the second input of the amplifier to the middle terminal of the second resistive voltage divider.

12. The method of claim 8, further comprising:
coupling a current limiting resistor between the second input of the amplifier and the second resistive voltage divider; and
coupling a bypass capacitor to the second input of the amplifier in parallel with the current limiting resistor.

13. A voltage-to-current converter for a device for measuring impedance of biological tissue, the device comprising a pair of electrodes for contacting the biological tissue, at least one single-ended amplitude modulation (AM) demodulator configured to demodulate an AC voltage and to generate a corresponding output voltage representing the impedance, the voltage-to-current converter comprising:
an amplifier to be coupled to the pair of electrodes and configured to drive an alternating current (AC) through the biological tissue and to sense an AC voltage, said amplifier having a first input, a second input, and an output;
a first resistive voltage divider coupled to the first input;
a second resistive voltage divider coupled to the second input;
a direct current (DC) filter capacitor coupled between the output of said amplifier and said second resistive voltage divider;
a current limiting resistor coupled between the second input of said amplifier and said second resistive voltage divider; and
a bypass capacitor coupled to the second input of said amplifier and in parallel with said current limiting resistor.

14. The voltage-to-current converter of claim 13, further comprising:
an output node; and
an input node configured to receive an AC drive voltage;
said first resistive voltage divider having a middle terminal and being coupled between the output node and the input node;
said second resistive voltage divider having a middle terminal and being coupled between a common terminal with one of the pair of electrodes and to the output node, and another one of the pair of electrodes coupled to the middle terminal.

15. The voltage-to-current converter of claim 14, wherein said first input of said amplifier is coupled to the middle node of said first resistive voltage divider, and said second input of said amplifier coupled to the middle terminal of the second resistive voltage divider.

16. The voltage-to-current converter of claim 14, wherein the second resistive voltage divider has a same voltage ratio as said first resistive voltage divider.

* * * * *